US00PP19892P2

(12) United States Plant Patent
van Nijnatten

(10) Patent No.: US PP19,892 P2
(45) Date of Patent: Apr. 7, 2009

(54) *CORNUS* PLANT NAMED 'CATO'

(50) Latin Name: *Cornus sanguinea*
Varietal Denomination: Cato

(75) Inventor: Andre van Nijnatten, Zunderi (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 320 days.

(21) Appl. No.: 11/494,115

(22) Filed: Jul. 27, 2006

(51) Int. Cl.
*A01H 5/00* (2006.01)

(52) U.S. Cl. ..... Plt./220
(58) Field of Classification Search ..... Plt./226, Plt./220
See application file for complete search history.

(56) References Cited

PUBLICATIONS

Sanders, C., Shedding light on *Cornus sanguinea*, 2005, Royal Horticultural Society (RHS) London, UK, Plantsman vol. 4 (4): p. 198–203, (Abstract only).*

* cited by examiner

*Primary Examiner*—Kent L Bell
(74) *Attorney, Agent, or Firm*—C. A. Whealy

(57) ABSTRACT

A new and distinct cultivar of *Cornus* plant named 'Cato', characterized by its low mounded plant habit; freely branching habit; dense and bushy appearance; leaves becoming rich yellow in color during the autumn; and yellow to red-colored stems.

1 Drawing Sheet

Botanical designation: *Cornus sanguinea.*
Cultivar denomination: 'Cato'.

BACKGROUND OF THE INVENTION

The present invention relates to a new and distinct cultivar of *Cornus,* grown as an ornamental shrub, botanically known as *Cornus sanguinea* and hereinafter referred to by the name 'Cato'.

The new *Cornus* is a product of a planned breeding program conducted by the Inventor in Zundert, The Netherlands. The objective of the breeding program was to develop new *Cornus* cultivars with improved growth habit and coloration.

The new *Cornus* originated from an open-pollination made during 1997 of the *Cornus sanguinea* cultivar Winter Flame, not patented, as the female, or seed, parent with an unknown selection of *Cornus sanguinea.* The new *Cornus* was discovered and selected by the Inventor from within the progeny of the stated open-pollination in a controlled environment in Zundert, The Netherlands in 1998.

Asexual reproduction of the new *Cornus* by softwood cuttings in a controlled environment in Zundert, The Netherlands since 1999, has shown that the unique features of this new *Cornus* are stable and reproduced true to type in successive generations.

SUMMARY OF THE INVENTION

The cultivar Cato has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cato'. These characteristics in combination distinguish 'Cato' as a new and distinct cultivar of *Cornus:*

1. Low mounded plant habit.
2. Freely branching habit; dense and bushy appearance.
3. Leaves becoming rich yellow in color during the autumn.
4. Yellow to red-colored stems.

Plants of the new *Cornus* differ from plants of the female parent, the cultivar Winter Flame, in the following characteristics:

1. Plants of the new *Cornus* are shorter and more mounded than plants of the cultivar Winter Flame.
2. Leaves of plants of the new *Cornus* develop more intense and attractive autumn coloration than leaves of plants of the cultivar Winter Flame.

Plants of the new *Cornus* can also be compared to plants of the cultivar Anne's Orange, not patented. Plants of the new *Cornus* differ from plants of the cultivar Anne's Orange in the following characteristics:

1. Plants of the new *Cornus* are shorter than plants of the cultivar Anne's Orange.
2. Plants of the new *Cornus* are more outwardly spreading than and not as upright as plants of the cultivar Anne's Orange.
3. Plants of the new *Cornus* have smaller leaves than plants of the cultivar Anne's Orange.

BRIEF DESCRIPTION OF THE PHOTOGRAPHS

The accompanying colored photographs illustrate the overall appearance of the new *Cornus,* showing the colors as true as it is reasonably possible to obtain in colored reproductions of this type. Colors in the photographs may differ slightly from the color values cited in the detailed botanical description which accurately describe the colors of the new *Cornus*.

The photograph at the top of the sheet comprises a side perspective view of a typical plant of 'Cato' grown during the summer in an outdoor nursery.

The photograph at the bottom of the sheet is a side perspective view of a typical plant of 'Anne's Orange' (left) and 'Cato' (right) grown during the early autumn in an outdoor nursery.

DETAILED BOTANICAL DESCRIPTION

The aforementioned photographs and following observations, measurements and values describe plants grown in Grand Haven, Mich., under commercial practice in an outdoor nursery. Plants had been growing for about three years when the photographs and description were taken. In the following description, color references are made to The Royal Horticultural Society Colour Chart, 1995 Edition, except where general terms of ordinary dictionary significance are used.

Botanical classification: *Cornus sanguinea* cultivar Cato.

Parentage:

*Female, or seed, parent.*—*Cornus sanguinea* cultivar Winter Flame, not patented.

*Male, or pollen parent.*—Unknown selection of *Cornus sanguinea,* not patented.

Propagation:

*Type.*—By softwood cuttings.

*Time to initiate roots.*—About 20 days at 24° C.

*Time to produce a rooted young plant.*—About three months at 24° C.

*Root description.*—Fine to thick; white in color.

*Rooting habit.*—Freely branching; dense.

Plant description:

*Plant form/habit.*—Low mounding subshrub; outwardly spreading form. Freely branching habit, about 62 lateral branches per plant; dense and bushy appearance. Moderately vigorous growth habit.

*Plant height.*—About 85 cm.

*Plant width* (*spread*).—About 2 meters.

*Lateral branches.*—Length: About 58 cm. Diameter: About 4 mm. Internode length: About 5.6 cm. Strength: Strong. Texture: Pubescent. Color: Towards the base, 12C; towards the apex, 45C.

Foliage description:

*Arrangement.*—Opposite, simple.

*Length.*—About 9.2 cm.

*Width.*—About 5.5 cm.

*Shape.*—Ovate.

*Apex.*—Acute.

*Base.*—Obtuse.

*Margin.*—Entire; undulate.

*Texture, upper surface.*—Smooth, glabrous.

*Texture, lower surface.*—Pubescent.

*Venation pattern.*—Pinnate.

*Color.*—Developing and fully developed leaves, upper surface: 144A; venation, 144A. During the autumn, color becoming closer to 12C. Developing and fully developed leaves, lower surface: 144A; venation, 157A.

*Petiole.*—Length: About 1.7 cm. Diameter: About 2 mm. Texture, upper and lower surfaces: Smooth, glabrous. Color, upper and lower surfaces: 157A.

Flower description: Flower initiation and development has not been observed on plants of the new *Cornus*.

Disease/pest resistance: Plants of the new *Cornus* have not been noted to be resistant to pathogens and pests common to *Cornus*.

Temperature tolerance: Plants of the new *Cornus* have been observed to tolerate temperatures from about −26° C. to about 35° C.

It is claimed:

1. A new and distinct *Cornus* plant named 'Cato' as illustrated and described.

* * * * *

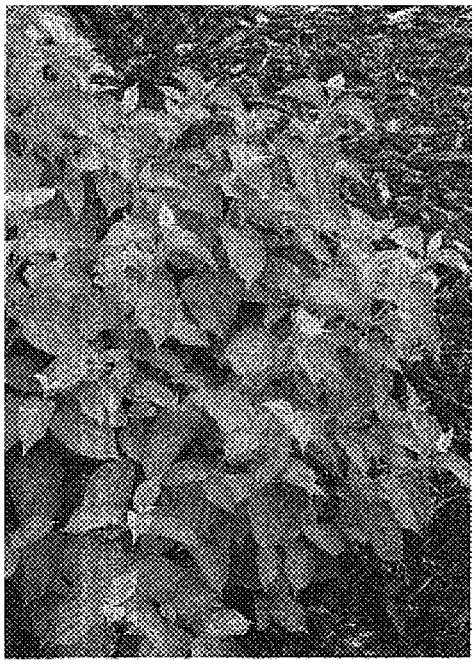
Photo A. Cornus s. 'Canto' in Summer
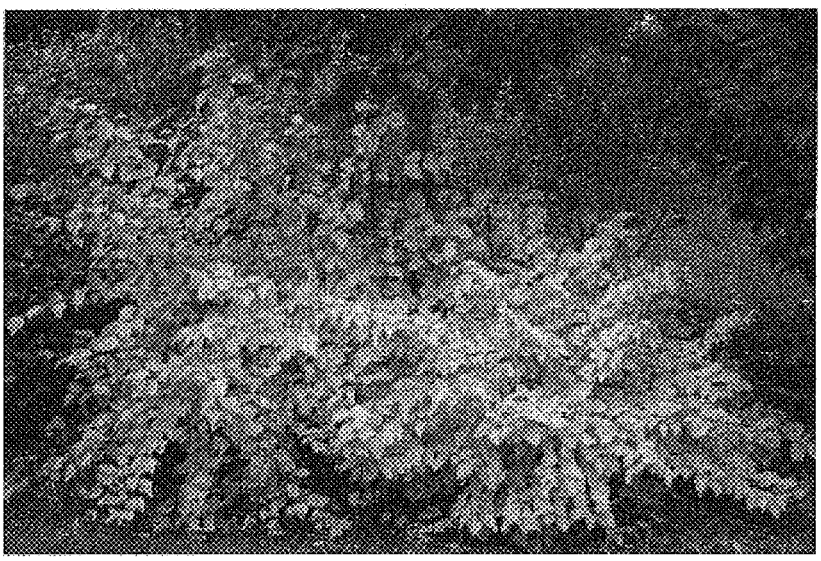
Photo B. (left) Cornus s. 'Anne's Orange' (right) C. 'Canto' in early autumn